(12) United States Patent
Perez (10) Patent No.: US 12,059,804 B2
(45) Date of Patent: Aug. 13, 2024

(54) BIDIRECTIONAL KINEMATIC MOUNT

(71) Applicant: MAKO Surgical Corp., Ft. Lauderdale, FL (US)

(72) Inventor: Timothy Wade Perez, Plantation, FL (US)

(73) Assignee: MAKO Surgical Corp., Weston, FL (US)

( * ) Notice: Subject to any disclaimer, the term of this patent is extended or adjusted under 35 U.S.C. 154(b) by 1078 days.

(21) Appl. No.: 16/881,475

(22) Filed: May 22, 2020

(65) Prior Publication Data

US 2020/0368898 A1 Nov. 26, 2020

Related U.S. Application Data

(60) Provisional application No. 62/851,426, filed on May 22, 2019.

(51) Int. Cl.
*A61B 34/37* (2016.01)
*A61B 90/00* (2016.01)
(Continued)

(52) U.S. Cl.
CPC ............ *B25J 9/1065* (2013.01); *A61B 34/37* (2016.02); *A61B 90/39* (2016.02); *B25J 9/0039* (2013.01);
(Continued)

(58) Field of Classification Search
CPC ........ B25J 9/0039; B25J 9/042; B25J 9/1065; A61B 34/37; A61B 34/20; A61B 2090/3945; A61B 17/15; A61B 50/20
See application file for complete search history.

(56) References Cited

U.S. PATENT DOCUMENTS

| 4,362,416 A | 12/1982 | Kaimo |
| 5,017,139 A | 5/1991 | Mushabac |

(Continued)

FOREIGN PATENT DOCUMENTS

| DE | 10335388 B4 | 6/2006 |
| EP | 1873666 A1 | 1/2008 |

(Continued)

OTHER PUBLICATIONS

English language abstract and machine-assisted English translation for DE 103 35 388 extracted from espacenet.com database on Oct. 11, 2017, 14 pages.

(Continued)

*Primary Examiner* — Tan-Uyen T Ho
*Assistant Examiner* — Bridget E. Rabaglia
(74) *Attorney, Agent, or Firm* — Howard & Howard Attorneys PLLC (57) ABSTRACT

A kinematic mounting key engageable with a kinematic mounting receiver is provided. The kinematic mounting key comprises a base kinematic element, a first protrusion, and a second protrusion. Each of the first protrusion and the second protrusion defines a clearance channel and comprises a kinematic element. The clearance channels and the kinematic elements are configured so that the kinematic mounting key is engageable with the kinematic mounting receiver in a first arrangement at six points of contact and in a second arrangement at six points of contact that are at least partially different from the six points of contact of the first arrangement.

18 Claims, 7 Drawing Sheets

(51) Int. Cl.
  *B25J 9/00*   (2006.01)
  *B25J 9/04*   (2006.01)
  *B25J 9/10*   (2006.01)
  *A61B 34/20*  (2016.01)

(52) U.S. Cl.
  CPC ....... *B25J 9/042* (2013.01); *A61B 2034/2063* (2016.02); *A61B 2090/3945* (2016.02)

(56) References Cited

U.S. PATENT DOCUMENTS

| | | |
|---|---|---|
| 5,142,930 A | 9/1992 | Allen et al. |
| 5,167,464 A | 12/1992 | Voellmer |
| 5,174,772 A | 12/1992 | Vranish |
| 5,566,681 A | 10/1996 | Manwaring et al. |
| 5,676,673 A | 10/1997 | Ferre et al. |
| 5,683,118 A | 11/1997 | Slocum |
| 5,748,827 A | 5/1998 | Holl et al. |
| 5,855,582 A | 1/1999 | Gildenberg |
| 5,987,960 A | 11/1999 | Messner et al. |
| 6,021,343 A | 2/2000 | Foley et al. |
| 6,052,611 A | 4/2000 | Yanof et al. |
| 6,066,141 A | 5/2000 | Dall et al. |
| 6,167,145 A | 12/2000 | Foley et al. |
| 6,190,395 B1 | 2/2001 | Williams |
| 6,193,430 B1 | 2/2001 | Culpepper et al. |
| 6,203,543 B1 | 3/2001 | Glossop |
| 6,226,548 B1 | 5/2001 | Foley et al. |
| 6,377,011 B1 | 4/2002 | Ben-Ur |
| 6,379,071 B1 | 4/2002 | Sorvino |
| 6,434,507 B1 | 8/2002 | Clayton et al. |
| 6,484,049 B1 | 11/2002 | Seeley et al. |
| 6,514,259 B2 | 2/2003 | Picard et al. |
| 6,517,484 B1 | 2/2003 | Wilk et al. |
| 6,529,765 B1 | 3/2003 | Franck et al. |
| 6,572,624 B2 | 6/2003 | U et al. |
| 6,719,757 B2 | 4/2004 | Neubauer et al. |
| 6,729,589 B2 | 5/2004 | Shelef |
| 6,738,657 B1 | 5/2004 | Franklin et al. |
| 6,746,172 B2 | 6/2004 | Culpepper |
| 6,856,828 B2 | 2/2005 | Cossette et al. |
| 6,893,447 B2 | 5/2005 | Dominguez et al. |
| 6,932,823 B2 | 8/2005 | Grimm et al. |
| 7,043,961 B2 | 5/2006 | Pandey et al. |
| 7,153,297 B2 | 12/2006 | Peterson |
| 7,153,308 B2 | 12/2006 | Peterson |
| 7,166,114 B2 | 1/2007 | Moctezuma De La Barrera et al. |
| 7,274,958 B2 | 9/2007 | Jutras et al. |
| 7,300,432 B2 | 11/2007 | Surma et al. |
| 7,302,288 B1 | 11/2007 | Schellengberg |
| 7,314,048 B2 | 1/2008 | Couture et al. |
| 7,366,561 B2 | 4/2008 | Mills et al. |
| 7,377,924 B2 | 5/2008 | Raistrick et al. |
| 7,419,492 B2 | 9/2008 | Yoon et al. |
| 7,458,977 B2 | 12/2008 | McGinley et al. |
| 7,477,926 B2 | 1/2009 | McCombs |
| 7,547,307 B2 | 6/2009 | Carson et al. |
| 7,558,617 B2 | 7/2009 | Vilsmeier |
| 7,641,660 B2 | 1/2010 | Lakin et al. |
| 7,646,899 B2 | 1/2010 | Fitzpatrick |
| 7,668,584 B2 | 2/2010 | Jansen |
| 7,688,998 B2 | 3/2010 | Tuma et al. |
| 7,725,162 B2 | 5/2010 | Malackowski et al. |
| 7,725,182 B2 | 5/2010 | Sutardja |
| 7,726,564 B2 | 6/2010 | Goldbach |
| 7,736,368 B2 | 6/2010 | Couture et al. |
| 7,753,910 B2 | 7/2010 | Ritland |
| 7,764,985 B2 | 7/2010 | McCombs et al. |
| 7,771,436 B2 | 8/2010 | Moctezuma De La Barrera et al. |
| 7,776,000 B2 | 8/2010 | Schaffrath et al. |
| 7,780,681 B2 | 8/2010 | Sarin et al. |
| 7,794,469 B2 | 9/2010 | Kao et al. |
| 7,881,770 B2 | 2/2011 | Melkent et al. |
| 7,925,328 B2 | 4/2011 | Urquhart et al. |
| 7,970,174 B2 | 6/2011 | Goldbach |
| 7,970,190 B2 | 6/2011 | Steinle et al. |
| 7,993,353 B2 | 8/2011 | Roeßner et al. |
| 8,021,369 B2 | 9/2011 | Curry |
| 8,066,961 B2 | 11/2011 | Costello, III et al. |
| 8,105,339 B2 | 1/2012 | Melkent et al. |
| 8,109,877 B2 | 2/2012 | Moctezuma De La Barrera et al. |
| 8,114,134 B2 | 2/2012 | Winslow et al. |
| 8,152,726 B2 | 4/2012 | Amiot et al. |
| 8,165,658 B2 | 4/2012 | Waynik et al. |
| 8,202,322 B2 | 6/2012 | Doty |
| 8,226,724 B2 | 7/2012 | Doty |
| 8,277,505 B1 | 10/2012 | Doty |
| 8,348,954 B2 | 1/2013 | Carls et al. |
| 8,357,165 B2 | 1/2013 | Grant et al. |
| 8,382,766 B2 | 2/2013 | Warkentine et al. |
| 8,386,022 B2 | 2/2013 | Jutras et al. |
| 8,457,719 B2 | 6/2013 | Moctezuma De La Barrera et al. |
| 8,460,277 B2 | 6/2013 | Suarez et al. |
| 8,469,965 B2 | 6/2013 | Neubauer et al. |
| 8,512,346 B2 | 8/2013 | Couture |
| 8,535,329 B2 | 9/2013 | Sarin et al. |
| 8,549,732 B2 | 10/2013 | Burg et al. |
| 8,611,985 B2 | 12/2013 | Lavallee et al. |
| 8,644,570 B2 | 2/2014 | Hartmann et al. |
| 8,657,809 B2 | 2/2014 | Schoepp |
| 8,672,490 B2 | 3/2014 | Shafer et al. |
| 8,709,017 B2 | 4/2014 | Pla ky et al. |
| 8,721,660 B2 | 5/2014 | Ulfarsson et al. |
| 8,747,419 B2 | 6/2014 | Solar et al. |
| 8,800,939 B2 | 8/2014 | Karsak et al. |
| 8,845,655 B2 | 9/2014 | Henderson et al. |
| 8,862,200 B2 | 10/2014 | Sherman et al. |
| 8,942,788 B2 | 1/2015 | Roger |
| 8,945,132 B2 | 2/2015 | Pla y et al. |
| 9,008,757 B2 | 4/2015 | Wu |
| 9,066,751 B2 | 6/2015 | Sasso |
| 9,082,319 B2 | 7/2015 | Shimada et al. |
| 9,085,401 B2 | 7/2015 | Shafer et al. |
| 9,095,376 B2 | 8/2015 | Pla ky et al. |
| 9,125,624 B2 | 9/2015 | Dekel et al. |
| 9,131,987 B2 | 9/2015 | Stefanchik et al. |
| 9,157,698 B2 | 10/2015 | Cosentino |
| 9,161,799 B2 | 10/2015 | Benson et al. |
| 9,495,509 B2 | 11/2016 | Amiot et al. |
| 10,537,394 B2 | 1/2020 | Strobl |
| 10,537,395 B2 | 1/2020 | Perez |
| 2003/0086748 A1 | 5/2003 | Culpepper |
| 2003/0135213 A1 | 7/2003 | LeHuec et al. |
| 2004/0068263 A1 | 4/2004 | Chouinard et al. |
| 2004/0127902 A1 | 7/2004 | Suzuki et al. |
| 2004/0171930 A1 | 9/2004 | Grimm et al. |
| 2005/0049485 A1 | 3/2005 | Harmon et al. |
| 2005/0109855 A1 | 5/2005 | McCombs |
| 2005/0124988 A1 | 6/2005 | Terrill-Grisoni et al. |
| 2005/0137599 A1 | 6/2005 | Masini |
| 2005/0187562 A1 | 8/2005 | Grimm et al. |
| 2005/0203528 A1 | 9/2005 | Couture et al. |
| 2005/0228387 A1 | 10/2005 | Paul |
| 2005/0277933 A1 | 12/2005 | Wall et al. |
| 2006/0015018 A1 | 1/2006 | Jutras et al. |
| 2006/0015119 A1 | 1/2006 | Plassky et al. |
| 2006/0052691 A1 | 3/2006 | Hall et al. |
| 2006/0052792 A1 | 3/2006 | Boettiger et al. |
| 2006/0142656 A1 | 6/2006 | Malackowski et al. |
| 2006/0161059 A1 | 7/2006 | Wilson |
| 2006/0195111 A1 | 8/2006 | Couture |
| 2006/0235290 A1 | 10/2006 | Gabriel et al. |
| 2006/0241405 A1 | 10/2006 | Leitner et al. |
| 2007/0233156 A1 | 10/2007 | Metzger |
| 2008/0027452 A1 | 1/2008 | Sheffer et al. |
| 2008/0114375 A1 | 5/2008 | von Jako |
| 2008/0183108 A1 | 7/2008 | Huber et al. |
| 2009/0024127 A1 | 1/2009 | Lechner et al. |
| 2009/0099445 A1 | 4/2009 | Burger |
| 2009/0118742 A1 | 5/2009 | Hartmann et al. |
| 2009/0163930 A1 | 6/2009 | Aoude et al. |
| 2009/0247863 A1 | 10/2009 | Proulx |
| 2009/0270928 A1 | 10/2009 | Stone et al. |
| 2009/0281417 A1 | 11/2009 | Hartmann et al. |

(56) References Cited

U.S. PATENT DOCUMENTS

| | | |
|---|---|---|
| 2009/0281421 A1 | 11/2009 | Culp et al. |
| 2009/0306499 A1 | 12/2009 | Van Vorhis et al. |
| 2010/0023062 A1 | 1/2010 | Faillace et al. |
| 2010/0063511 A1 | 3/2010 | Plassky et al. |
| 2010/0094358 A1 | 4/2010 | Moore et al. |
| 2010/0125286 A1 | 5/2010 | Wang et al. |
| 2010/0160932 A1 | 6/2010 | Gschwandtner et al. |
| 2010/0192961 A1 | 8/2010 | Amiot et al. |
| 2011/0004259 A1 | 1/2011 | Stallings et al. |
| 2011/0098553 A1 | 4/2011 | Robbins et al. |
| 2011/0160572 A1 | 6/2011 | McIntosh |
| 2011/0166446 A1 | 7/2011 | Whitmore et al. |
| 2012/0016427 A1 | 1/2012 | Stindel et al. |
| 2012/0109228 A1 | 5/2012 | Boyer et al. |
| 2012/0143048 A1 | 6/2012 | Finlay |
| 2013/0053895 A1 | 2/2013 | Stoll et al. |
| 2013/0096573 A1 | 4/2013 | Kang et al. |
| 2013/0123580 A1 | 5/2013 | Peters et al. |
| 2013/0165947 A1 | 6/2013 | Nguyen et al. |
| 2013/0261783 A1 | 10/2013 | Paon et al. |
| 2013/0331686 A1 | 12/2013 | Freysinger et al. |
| 2014/0049629 A1 | 2/2014 | Siewerdsen et al. |
| 2014/0200621 A1 | 7/2014 | Malackowski et al. |
| 2014/0236159 A1 | 8/2014 | Haider et al. |
| 2014/0276943 A1 | 9/2014 | Bowling et al. |
| 2014/0364858 A1 | 12/2014 | Li et al. |
| 2015/0031982 A1 | 1/2015 | Piferi et al. |
| 2015/0088108 A1 | 3/2015 | Tyc et al. |
| 2015/0173911 A1 | 6/2015 | Doty |
| 2015/0182285 A1 | 7/2015 | Yen et al. |
| 2015/0182293 A1 | 7/2015 | Yang et al. |
| 2015/0209119 A1 | 7/2015 | Theodore et al. |
| 2015/0257851 A1 | 9/2015 | Plassky et al. |
| 2015/0265769 A1 | 9/2015 | Bratbak et al. |
| 2015/0282735 A1 | 10/2015 | Rossner |
| 2015/0309187 A1 | 10/2015 | Shafer et al. |
| 2016/0249988 A1 | 9/2016 | Pfeifer et al. |
| 2017/0333136 A1 | 11/2017 | Hladio et al. |
| 2017/0340395 A1* | 11/2017 | Perez ............... A61B 34/20 |

FOREIGN PATENT DOCUMENTS

| | | |
|---|---|---|
| JP | 2008538184 A | 10/2008 |
| JP | 2011515163 A | 5/2011 |
| WO | 02080773 A1 | 10/2002 |
| WO | 2006091494 A1 | 8/2006 |
| WO | 2007014470 A2 | 2/2007 |
| WO | 2007038135 A2 | 4/2007 |
| WO | 2008104548 A1 | 9/2008 |
| WO | 2008113008 A2 | 9/2008 |
| WO | 2008133615 A1 | 11/2008 |
| WO | 2009117832 A1 | 10/2009 |
| WO | 2010055193 A1 | 5/2010 |
| WO | 2012103407 A1 | 8/2012 |
| WO | 2012127353 A1 | 9/2012 |
| WO | 2013091112 A1 | 6/2013 |
| WO | 2013177334 A1 | 11/2013 |
| WO | 2014091053 A1 | 6/2014 |
| WO | 2014139022 A1 | 9/2014 |
| WO | 2014198784 A1 | 12/2014 |
| WO | 2015013518 A1 | 1/2015 |
| WO | 2015067743 A2 | 5/2015 |
| WO | 2015090434 A1 | 6/2015 |
| WO | 2015150877 A1 | 10/2015 |

OTHER PUBLICATIONS

English language abstract and machine-assisted English translation for WO 2008/104548 extracted from espacenet.com database on Oct. 12, 2017, 20 pages.

English language abstract for WO 2014/091053 and machine-assisted English translation for equivalent ES 2477140 of WO 2014/091053 extracted from espacenet.com database on Oct. 26, 2017, 10 pages.

English language abstract for WO 2015/067743 extracted from espacenet.com database on Oct. 12, 2017, 2 pages.

English language abstract for JP 2008-538184 extracted from espacenet.com database on Jun. 18, 2018, 2 pages.

English language abstract for JP 2011-515163 extracted from espacenet.com database on Jun. 18, 2018, 2 pages.

English language abstract for EP 1 873 666 A1 extracted from the www.espacenet.com database on Dec. 12, 2018.

\* cited by examiner

BIDIRECTIONAL KINEMATIC MOUNT

RELATED APPLICATIONS

This application claims priority to and the benefit of U.S. Provisional Application No. 62/851,426, filed on May 22, 2019, the entire contents of which are hereby incorporated by reference.

BACKGROUND

Navigation systems assist users in locating objects. For instance, navigation systems are used in industrial, aerospace, and medical applications. In the medical field, surgical navigation systems assist surgeons in locating surgical instruments and anatomy for the purpose of accurately placing the surgical instruments relative to the anatomy.

Navigation systems may employ light signals, sound waves, magnetic fields, radio frequency signals, etc. in order to track the position and/or orientation of objects. Often the navigation system comprises tracking devices attached to the objects being tracked. A localizer cooperates with tracking elements on the tracking devices to determine positions of the tracking elements, and ultimately to determine a position and orientation of the objects. The navigation system monitors movement of the objects via the tracking devices. Often, there is a need for the tracking devices to be releasably attached to the objects. However, when the tracking device is removed from the object and then reattached, its positional relationship with respect to the object usually changes, requiring recalibration or re-registration of the tracking device to the object.

SUMMARY

A kinematic mounting key engageable with a kinematic mounting receiver is disclosed. The kinematic mounting key comprises a base kinematic element and a first protrusion. The first protrusion comprises a first pedestal having a proximal end and a distal end, the proximal end coupled to the base kinematic element. The first protrusion further comprises a first kinematic element coupled to the distal end of the first pedestal, and a first clearance channel defined within the first pedestal and within a portion of the first kinematic element. The kinematic mounting key further comprises a second protrusion. The second protrusion comprises a second pedestal having a proximal end and a distal end, the proximal end coupled to the base kinematic element. The second protrusion further comprises a second kinematic element coupled to the distal end of the second pedestal, and a second clearance channel defined within the second pedestal and within a portion of the second kinematic element.

A kinematic mounting assembly is also disclosed. The kinematic mounting assembly comprises a kinematic mounting receiver defining a cavity and having a first pair and a second pair of constraint surfaces accessible in the cavity. The kinematic mounting assembly further comprises a kinematic mounting key engageable with the kinematic mounting receiver and comprising a base kinematic element, a first protrusion comprising a first pedestal comprising a proximal end and a distal end, the proximal end coupled to said base kinematic element. The first protrusion further comprises a first kinematic element coupled to the distal end of the first pedestal and comprising a first clearance channel defined within the first pedestal and within a portion of the first kinematic element. The kinematic mounting key further comprises a second protrusion comprising a second pedestal comprising a proximal end and a distal end, the proximal end coupled to the base kinematic element, a second kinematic element coupled to the distal end of the second pedestal, and comprising a second clearance channel defined within the second pedestal and within a portion of the second kinematic element.

A surgical assembly is also disclosed. The surgical assembly comprises a first surgical component comprising a kinematic mounting receiver defining a cavity and having a first pair and a second pair of constraint surfaces accessible in the cavity. The surgical assembly further comprises a second surgical component comprising a kinematic mounting key engageable with the kinematic mounting receiver. The kinematic mounting key comprises a base kinematic element and a first protrusion. The first protrusion comprises a first pedestal comprising a proximal end and a distal end, the proximal end coupled to the base kinematic element, a first kinematic element coupled to the distal end of the first pedestal and comprising a first clearance channel defined within the first pedestal and within a portion of the first kinematic element. The kinematic mounting key further comprises a second protrusion, which comprises a second pedestal. The second pedestal comprises a proximal end and a distal end, the proximal end coupled to the base kinematic element, a second kinematic element coupled to the distal end of the second pedestal and comprising a second clearance channel defined within the second pedestal and within a portion of the second kinematic element.

BRIEF DESCRIPTION OF THE DRAWINGS

Other advantages of the present invention will be readily appreciated as the same becomes better understood by reference to the following detailed description when considered in connection with the accompanying drawings.

DETAILED DESCRIPTION

Figure 1:
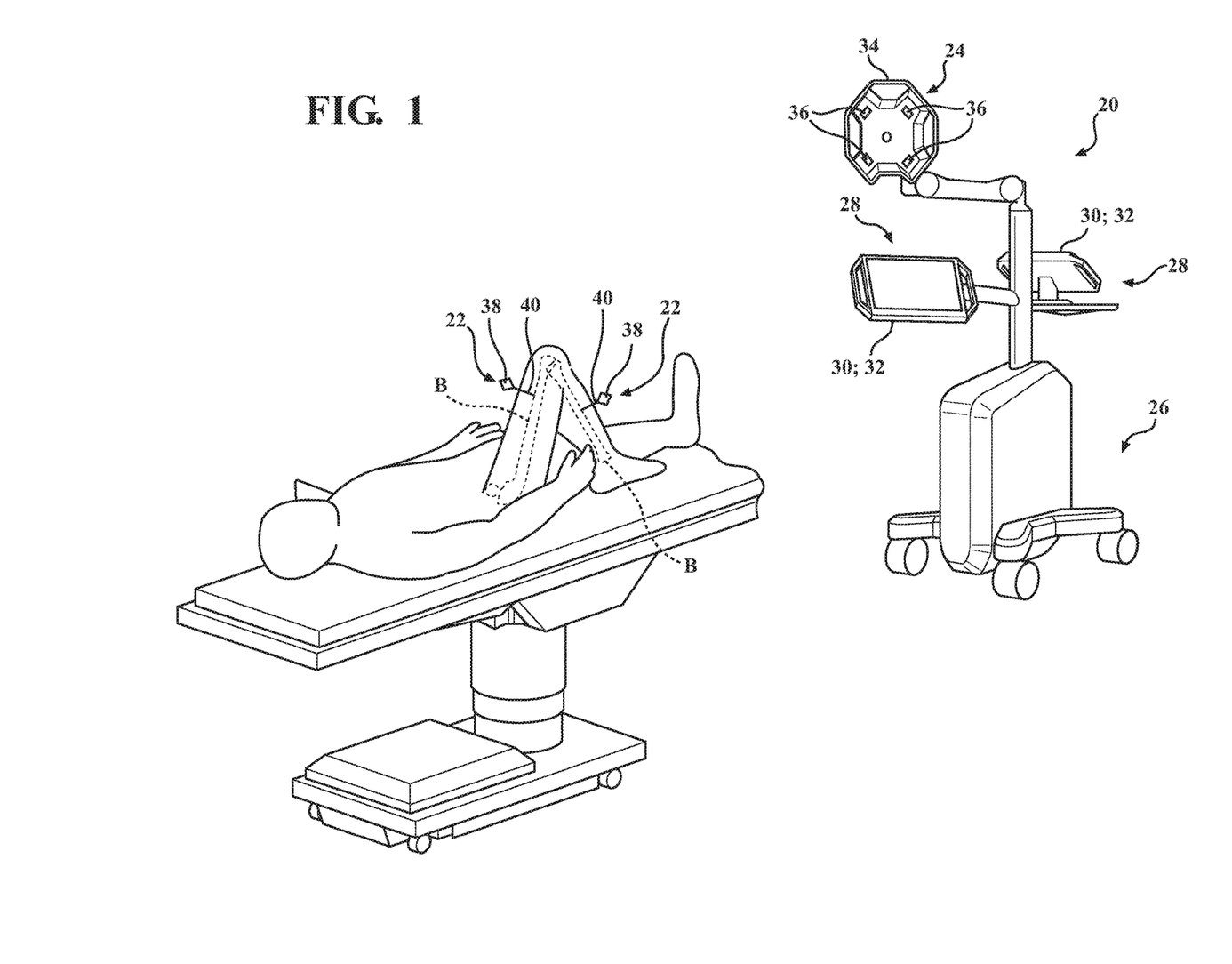
FIG. 1 is a perspective view of a surgical navigation system and two tracker assemblies being used in conjunction with a patient.

With reference to the Figures, wherein like numerals indicate like parts throughout the several views, a navigation system 20 is illustrated. The navigation system 20 is shown in a surgical setting, such as an operating room of a medical facility. The navigation system 20 is configured to, among other things, track movement of various objects, such as surgical tools, a pointer, and parts of a patient's body B (e.g., bones or other anatomy). The navigation system 20 is able to monitor, track, and/or determine changes in relative position and/or orientation of one or more parts of the patient's body B, within a common coordinate system by utilizing various types of trackers 22 (e.g., multiple degree-of-freedom optical, inertial, and/or ultrasonic sensing devices), anatomical computer models (e.g., magnetic resonance imaging scans of the patient's anatomy), data from previous surgical procedures and/or previously-performed surgical techniques, and the like. To this end, the navigation system 20 employs a localizer 24 configured to sense the position and/or orientation of trackers 22 within a localizer coordinate system. A navigation controller (not shown) is disposed in communication with the localizer 24 and gathers position and/or orientation data for each tracker 22 sensed within a field of view of the localizer 24 in the localizer coordinate system.

In the representative example illustrated herein, the navigation controller and the localizer 24 are supported on a mobile cart 26. The mobile cart 26 also supports a user interface, generally indicated at 28, to facilitate operation of the navigation system 20 by displaying information to, and/or by receiving information from, the surgeon or another user. The user interface 28 is disposed in communication with the navigation system 20 and may comprise one or more output devices 30 (e.g., monitors, indicators, display screens, and the like) to present information to the surgeon or other users (e.g., images, video, data, graphics, navigable menus, and the like), and one or more input devices 32 (e.g., buttons, touch screens, keyboards, mice, gesture or voice-based input devices, and the like). One type of mobile cart 26 and user interface 28 that may be utilized with this type of navigation system 20 is described in U.S. Pat. No. 7,725,162 entitled "Surgery System", the disclosure of which is hereby incorporated by reference in its entirety.

The navigation system 20 comprises at least one tracker 22 firmly affixed to the object that is to be tracked. The localizer 24 can sense the position and/or orientation of a multiple number of trackers 22 to track a corresponding multiple number of objects within the localizer coordinate system. By way of example, trackers 22 may comprise a first patient tracker assembly, a second patient tracker assembly, as well as additional patient trackers, trackers for additional medical and/or surgical tools such as a pointer tracker coupled to a pointer, and the like.

With continued reference to FIG. 1, a first tracker 22 is firmly affixed to one bone of the patient's body B at or adjacent to a surgical site (e.g., to the femur near the knee), and a second tracker 22 is firmly affixed to a different bone (e.g., to a portion of the tibia). While not shown in detail, the trackers 22 can be coupled to a number of different bones in the patient's body in various ways, such as by threaded engagement, clamping, or by other techniques. Similarly, multiple trackers 22 may be coupled to the same bone B (such as the trackers 22 partially shown in FIG. 2). Various trackers 22 may be firmly affixed to different types of tracked objects (e.g., discrete bones, tools, pointers, and the like) in a number of different ways.

The position of the trackers 22 relative to the objects or anatomy to which they are attached can be determined by known registration techniques. For example, the position of the trackers 22 relative to the portions of the patient's body to which they are attached can be accomplished with various forms of point-based registration, such as where a distal tip of a pointer is used to engage against specific anatomical landmarks (e.g., touching specific portions of bone) or is used to engage several parts of a bone for surface-based registration as the localizer 24 monitors the position and orientation of the pointer. Conventional registration techniques can then be employed to correlate the pose of the trackers 22 to the patient's anatomy (e.g., to each of the femur and the acetabulum). Other types of registration are also possible. Position and/or orientation data may be gathered, determined, or otherwise handled by the navigation controller using a number of different registration/navigation techniques to determine coordinates of each tracker 22 within the localizer coordinate system.

In the illustrated example, the localizer 24 is an optical localizer and includes a camera unit 34 with one or more optical sensors 36. The navigation system 20 employs the optical sensors 36 of the camera unit 34 to sense the position and/or orientation of the trackers 22 within the localizer coordinate system. The trackers 22 may be further defined as tracker assemblies 22. As illustrated herein, the tracker assemblies 22 each employ a tracker head 38 with markers that can be sensed by the optical sensors 36 of the camera unit 34. One example of a navigation system 20 of this type is described in U.S. Pat. No. 9,008,757 entitled "Navigation System Including Optical and Non-Optical Sensors," the disclosure of which is hereby incorporated by reference in its entirety.

In the representative example illustrated herein, the markers are active markers, which emit light that is sensed by the optical sensors 36. More specifically, each tracker head 38 has at least three active markers for transmitting light signals to the optical sensors 36 of the localizer 24. The active markers can be, for example, light emitting diodes (LEDs) transmitting light signals, such as infrared light. In some examples, the light signals from the LEDs are fired at different frequencies for each tracker assembly 22. Each of the LEDs may be connected to a tracker controller (not shown) of the associated tracker assembly 22.

In other examples, the trackers 22 may employ passive markers (e.g., reflectors), which reflect light emitted from the camera unit 34 or another light source. Although one example of the navigation system 20 is illustrated throughout the drawings, the navigation system 20 may have any other suitable configuration for monitoring trackers 22, which may be of various types and configurations. For example, the navigation system 20 may comprise other types of localizers 24 and/or markers.

In some examples, the navigation system 20 and/or the localizer 24 may be radio frequency (RF) based. Here, the trackers 22 may comprise RF emitters or transponders, which may be passive or may be actively energized. Alternatively, in some examples, the navigation system 20 and/or localizer 24 may be electromagnetically (EM) based. For example, the navigation system 20 may comprise an EM transceiver coupled to the navigation controller and/or to another computing device, controller, and the like. Here, the trackers 22 may comprise EM components attached thereto (e.g., various types of magnetic trackers, electromagnetic trackers, inductive trackers, and the like), which may be passive or may be actively energized.

Figure 2:
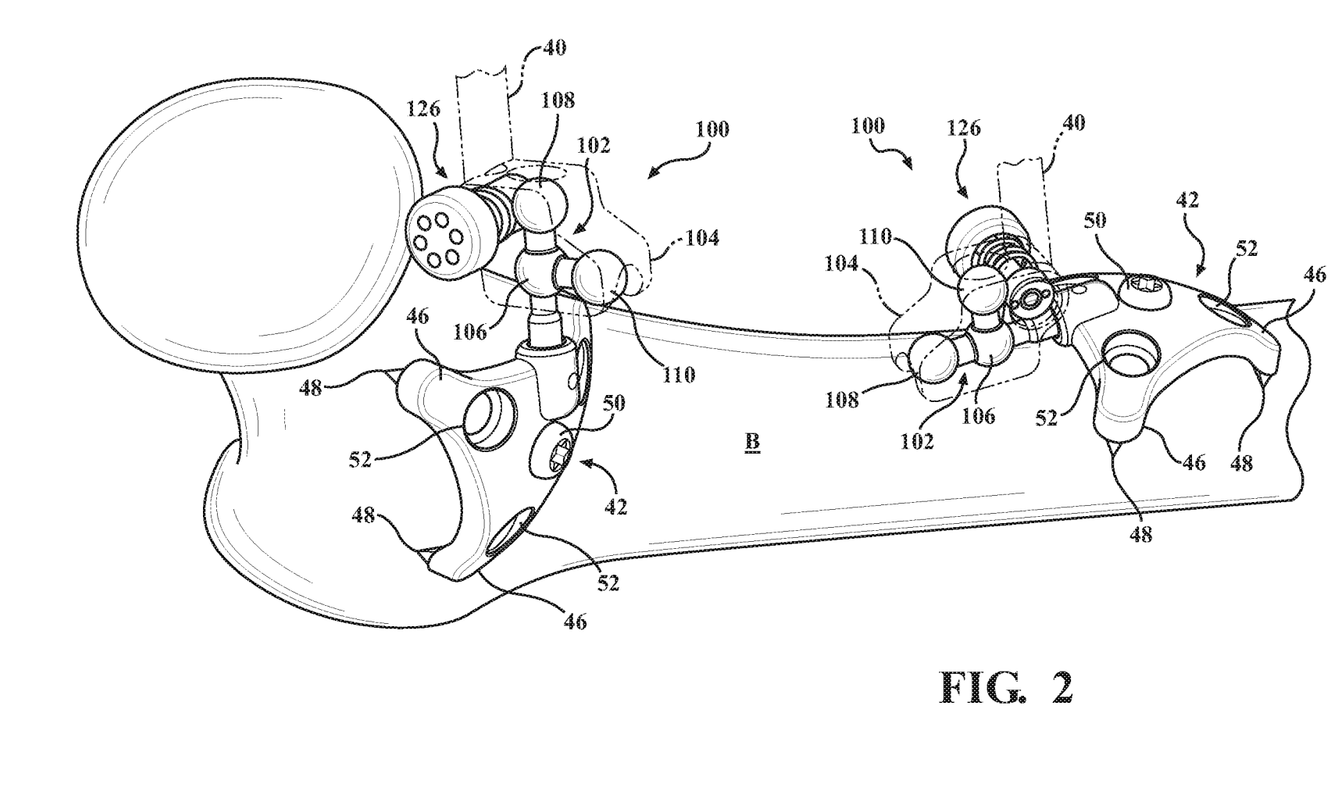
FIG. 2 is an enlarged perspective view of two kinematic mounting assemblies being used in conjunction with a bone plate and shown attached to the patient.
Figure 3:
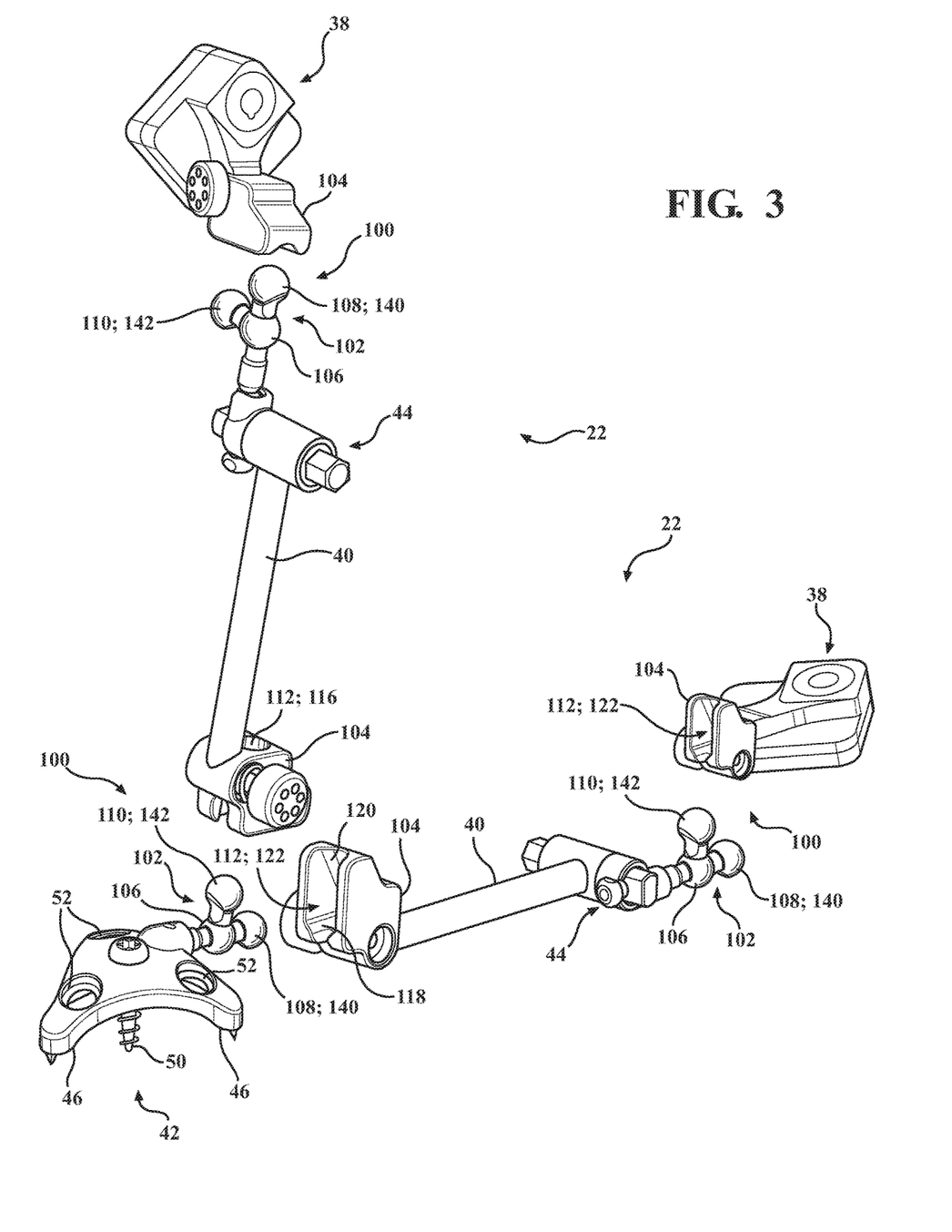
FIG. 3 is a perspective view of a tracker assembly with a kinematic mounting receiver shown spaced from a kinematic mounting key in two mounting orientations.

Referring to FIGS. 2 and 3, the tracker assembly 22 further comprises an extension link 40, and a bone plate 42. The extension link 40 locates the tracker head 38 away from the object that is to be tracked. The bone plate 42 is used to firmly affix the tracker assembly 22 to one of the patient's bones B during a surgical procedure.

As illustrated throughout the drawings, the extension link 40 is shown as an elongated rod having a circular cross section extending between a first end and a second end. The extension link 40 may extend along a path that is curved or angled such that any obstructions between the first and second ends are avoided. The path may be suitable to place the tracker head 38 away from the surgical site of interest so that the tracker head 38 remains out of the way of the surgical site. The extension link 40 may be any suitable length or shape, such as U-shaped, C-shaped, S-shaped, or straight. Furthermore, the extension link 40 may have any suitable cross section shape, such as rectangular or hexagonal, or structural shapes, such as X-shaped or tubular.

In some examples, one or both of the ends of the extension link 40 may comprise an adjustable mount 44 that is usable by the surgeon to aim the tracker head 38 prior to registration of the tracker 22 during a surgical procedure. The adjustable mount 44 affords the surgeon increased adaptability of the tracker assembly 22 when placing the extension link 40 to avoid obstructions or other anatomy.

The bone plate 42 comprises three arms 46 each having a barb 48 to pierce the bone B and prevent the bone plate 42 from moving relative to the bone B. A bone screw 50 may be used in combination with the bone plate 42, which defines an aperture 52 to receive the screw 50 in order to anchor the bone plate 42 to the bone B. The screw 50 is threaded into the bone B and draws the barbs 48 of the bone plate 42 into engagement with the bone B. The screw 50 may be placed in alternative apertures 52 of the bone plate 42 or multiple screws 50 may be employed in multiple apertures 52 to secure the bone plate 42.

During a surgical procedure, a need may arise to remove a tracker 22, or portion thereof, from the object to be tracked. For example, the tracker head 38 may limit the surgeon's access to a particular area of the surgical site, or hinder the procedure in other ways. In the scenario where the tracker head 38 has been disconnected from the tracked object, the position of the tracked object is unknown until the tracker head 38 is reconnected. When the tracker head 38 is reconnected, the surgical navigation system 20 can resume tracking the object. If the tracker head 38 is not reconnected to the tracked object in the same relative position, the tracked object's position may be inaccurate.

Coupling the tracker head 38 to the tracked object, bone B, in the same relative position involves kinematically constraining each of the six degrees-of-freedom in a repeatable manner. Each degree of freedom is constrained with a single point of contact, which avoids over or under-constraining the assembly. Repeatably de-coupling and coupling the tracker head 38 may be achieved using a tracker 22 with a kinematic connector assembly. One example of a tracker 22 of this type is described in U.S. Pat. No. 10,537, 395 entitled "Navigation tracker with kinematic connector assembly", the disclosure of which is hereby incorporated by reference in its entirety.

With continued reference to FIGS. 2 and 3, a kinematic mounting assembly 100 is used to repeatably couple the tracker head 38 to the extension link 40 in either a first arrangement or a second arrangement throughout the surgical procedure. Each time the tracker head 38 is coupled to the extension link 40 in the first arrangement, the tracker head 38 and the extension link 40 are in the same relative position. Similarly, each time the tracker head 38 is coupled to the extension link 40 in the second arrangement, the tracker head 38 and the extension link 40 are in the same relative position. The kinematic mounting assembly 100 allows the tracker head 38 to be disconnected from and repeatably connected to either the extension link 40 or the bone plate 42 without requiring the navigation system 20 to be recalibrated and/or the tracker assembly 22 to be re-registered to the object. Likewise, the tracker head 38 and the extension link 40 could be disconnected from, and connected to, the bone plate 42 as a unit without requiring the navigation system 20 to be recalibrated or the tracker assembly 22 to be re-registered to the object. At least one kinematic mounting assembly 100 is used to couple the tracker head 38 and the bone plate 42 to either end of the extension link 40.

In order to facilitate connection and removal of components of the tracker assembly 22, each of the kinematic mounting assemblies 100 shown in FIGS. 2 and 3 comprises a kinematic mounting key 102 and a kinematic mounting receiver 104. The kinematic mounting key 102 is configured to be secured in engagement with the kinematic mounting receiver 104 in a first arrangement and in a second arrangement. The kinematic mounting key 102 comprises a triplicity of kinematic elements 106, 108, 110 to position the kinematic mounting key 102 in the kinematic mounting receiver 104.

In the example shown, the tracker head 38 is coupled to a first end of the extension link 40 using a first kinematic mounting assembly 100. The bone plate 42 is coupled to a second end of the extension link 40 using a second kinematic mounting assembly 100. In some instances, the second kinematic mounting assembly 100 is the same as the first kinematic mounting assembly 100, such that components from the first kinematic mounting assembly 100 are interchangeable with components from the second kinematic mounting assembly 100, and vice versa. In this way, the tracker head 38 may be coupled directly to the bone plate 42 such that the tracker assembly 22 only comprises one kinematic mounting assembly 100.

Here, the extension link 40 comprises a key 102 coupled to the adjustable mount 44 at the first end, and a receiver 104 affixed to the second end. The tracker head 38 comprises another receiver 104 and the bone plate 42 comprises another key 102. The key 102 at the first end of the extension link 40 is engageable with the receiver 104 on the tracker head 38 to couple the tracker head 38 to the extension link 40. The key 102 on the bone plate 42 is engageable with the receiver 104 at the second end of the extension link 40 to couple the bone plate 42 to the extension link 40.

In some examples, the kinematic mounting assembly 100 is constructed from a metal, such as a surgical grade stainless steel. However, other materials may be used in the construction of the kinematic mounting assembly 100, such as metals, polymers, ceramics, and composites thereof. These materials may be plated, coated, or otherwise treated in order to modify physical characteristics of the material, such as biocompatibility, hardness, friction, etc.

As previously discussed, the first and second kinematic mounting assemblies 100 are interchangeable. Any key 102 is compatible with any receiver 104 such that tracker heads 38, extension links 40, bone plates 42, and other accessories may be used interchangeably as needed. For example, as mentioned above, the key 102 on the bone plate 42 is engageable with the receiver 104 on the tracker head 38 to couple the bone plate 42 directly to the tracker head 38.

Furthermore, while the tracker head 38 comprises the receiver 104, the bone plate 42 comprises the key 102, and the extension link 40 comprises both the key 102 and the receiver 104, each of the tracker head 38, the extension link 40, and the bone plate 42 can comprise either of the key 102 or the receiver 104 in any combination, such that various configurations of the tracker assembly 22 are possible. For example, the tracker head 38 may comprise the key 102 and the extension link 40 may comprise the receiver 104. Alternatively, the extension link 40 may comprise two receivers 104 in order to prevent the tracker head 38 from being coupled to the bone plate 42 and vice versa.

In general, an object that is a rigid body has six degrees of freedom in 3-dimensional space: three translational degrees of freedom along axes X, Y, Z, and three rotational degrees of freedom through rotation about the axes X, Y, Z, known as pitch, roll, and yaw. In order to control the position and orientation of a rigid body, all six degrees of freedom must be constrained. The rigid body can be constrained in one degree of freedom at one point of contact with a second rigid body. Therefore, two rigid bodies with exactly six points of contact will be constrained in all six degrees of freedom. Here, the kinematic mounting assembly 100 is able to repeatably couple the key 102 to the receiver 104 in the same relative position by constraining all six degrees of freedom. The kinematic mounting assembly 100 allows the key 102 to be disconnected from and repeatably connected to the receiver 104 without requiring the navigation system 20 to be recalibrated and/or the tracker assembly 22 to be re-registered to the object.

As previously discussed, it is desirable for the position of the object, in this case the patient's bones B, to be tracked throughout the duration of a surgical procedure. While it may be unavoidable to occasionally remove a tracker 22 or tracker head 38 in order to facilitate access to the surgical site, it is advantageous to position or reposition the tracker 22 so as to reduce the likelihood that its removal is necessary. Further, adaptability of the tracker assembly 22 is advantageous by allowing the tracker assembly 22 to be affixed to the object in an orientation that reduces obstruction to the surgeon and other users. In some situations, the orientation in which the bone plate 42 is secured to the patient may prevent the surgeon from placing the tracker head 38 in a non-obstructing position. By providing multiple arrangements for the kinematic mounting assembly 100 to couple each component of the tracker assembly 22, the surgeon is afforded greater flexibility when positioning each component at the beginning of the surgical procedure.

Adaptability of the tracker assembly 22 is advantageously promoted by the kinematic mounting assembly 100, which allows the kinematic mounting key 102 to be kinematically constrained with the kinematic mounting receiver 104 in more than one discrete position. Here, the kinematic mounting key 102 is engageable with the kinematic mounting receiver 104 in a first arrangement and in a second arrangement. FIG. 2 shows two tracker assemblies 22, one tracker assembly 22 is configured with the extension link 40 coupled to the bone plate 42 in the first arrangement, and another tracker assembly 22 is configured with the extension link 40 coupled to the bone plate 42 in the second arrangement. In the exemplary surgical procedure illustrated here, it is advantageous for both of the extension links 40 to be oriented in generally the same direction (i.e. up, or toward the top of the page). Due to the particular features of the patient's bone B, each of the bone plates 42 is affixed in a different orientation. By coupling one extension link 40 to one of the bone plates 42 in the first arrangement and another extension link 40 to the other bone plate 42 in the second arrangement, both extension links 40 can be oriented as desired.

More specifically, when a surgeon is affixing a bone plate 42 to a patient, the number of viable positions and/or orientations may be limited by factors such as the type of surgery being performed, the patient's individual anatomy, the surgeon's preferences, etc. If the extension link 40 can only be coupled to the bone plate 42 in a single orientation, the position of the bone plate 42 may result in sub-optimal placement of the tracker head 38 (i.e. out of view of the localizer 24). A kinematic mounting assembly 100 that permits the extension link 40 to be coupled to the bone plate 42 in multiple orientations may increase the number of positions that the bone plate 42 can be affixed to the bone B that will result in an acceptable tracker head 38 placement, or may aid optimization of tracker head 38 placement. Further, the navigation system 20 may be programmed to recognize both arrangements of the tracker assembly 22, thereby allowing the surgeon to alternate between each arrangement during the procedure as necessary.

FIG. 3 shows an exploded view of the two arrangements of the tracker assembly 22; two extension links 40 and two tracker heads 38 are shown spaced from the same bone plate 42. One of the extension links 40 and one of the tracker heads 38 are shown spaced from the bone plate 42 in the first arrangement and the other extension link 40 and tracker head 38 are shown spaced from the bone plate 42 in the second arrangement. Because the tracker head 38 and the extension link 40 can be coupled to the bone plate 42 in the first arrangement and the second arrangement, each tracker assembly 22 can be utilized in orientations that may have been previously unavailable. In this way the number of unique parts that may normally be kept for use during a surgical procedure can be reduced. For example, a kit of parts provided for a surgical procedure may contain three "vertical" extension links and three "horizontal" extension links some of which may not be used during that procedure. Alternatively, a kit of parts containing four extension links 40 usable in both the "vertical" and "horizontal" configuration may be provided without limiting usability.

Referring now to FIGS. 8-11, the receiver 104 of the kinematic mounting assembly 100 is shown. The receiver 104 defines a cavity 112 for receiving the key 102. The cavity 112 is defined, at least partially, by a plurality of constraint surfaces 114 accessible in the cavity 112. The constraint surfaces 114 define three channels 116, 118, 120 to receive the key 102 in the cavity 112. A first channel 116 and a second channel 118 extend through the cavity 112 and are substantially parallel to one another. A third channel 120 intersects the first channel 116 at an angle θ (see FIG. 9). The angle θ is approximately 120°, but other angles such as 45°, 60°, and 240° are also possible. As illustrated, the second and third channels 118, 120 terminate at a mouth portion 122 of the cavity 112. The mouth portion 122 is tapered such that the cavity 112 reduces in size further into the receiver 104. A preload bore 124 is further defined in the receiver 104 and extends therethrough. The preload bore 124 intersects with the second channel 118 in the cavity 112.

The constraint surfaces 114 of the receiver 104 define each channel 116, 118, 120 such that at least one constraint surface 114 in each channel 116, 118, 120 contacts one of the kinematic elements 106, 108, 110 at only two points. The channels 116, 118, 120 may each be defined by two planar constraint surfaces 114. The two planar surfaces may be joined by a third surface that does not contact the kinematic elements 106, 108, 110. In the present example, the channels 116, 118, 120 are substantially trapezoidal with two constraint surfaces 114 interconnected by a third non-contacting surface. The constraint surfaces 114 may also intersect such that the channels 116, 118, 120 form a V-shape. Each channel 116, 118, 120 may further define a single constraint surface, such as a curved U-shape, arch shape, or other arcuate shape of which two contact points are made.

Figure 10:
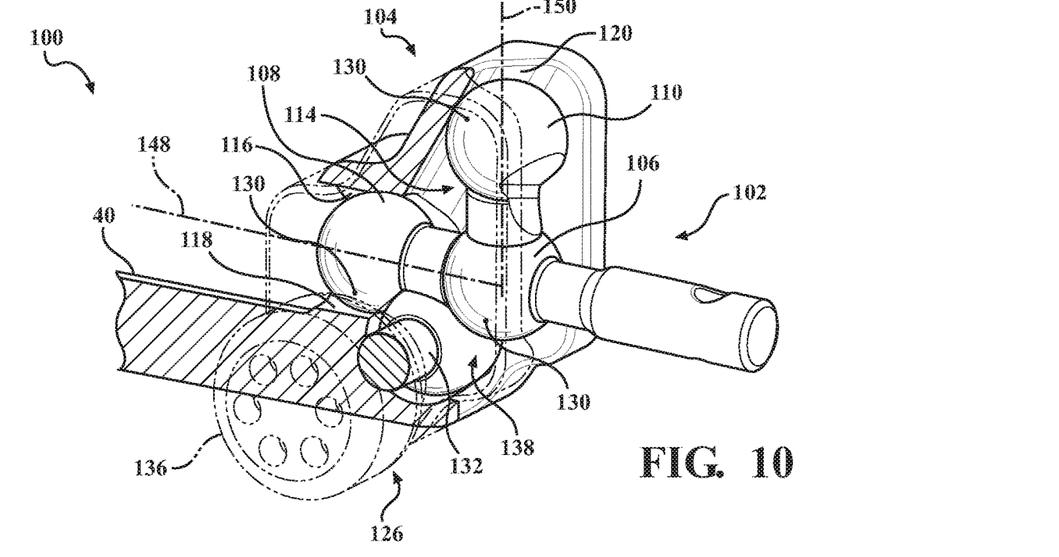
FIG. 10 is a cross-sectional perspective view of the kinematic mounting key engaged in a first position with the kinematic mounting receiver of FIG. 8 with the kinematic mounting receiver shown partially in phantom.
Figure 11:
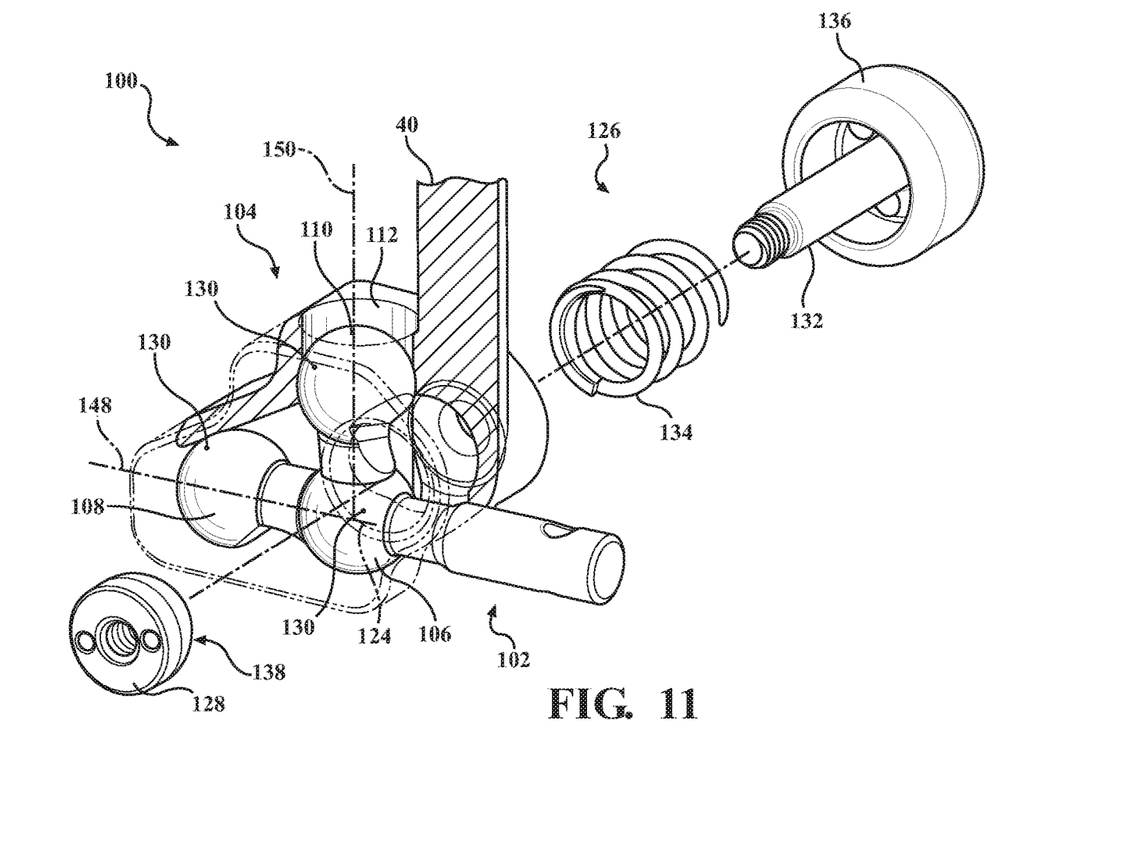
FIG. 11 is an exploded cross-sectional perspective view of the kinematic mounting key engaged in a second position with the kinematic mounting receiver shown partially in phantom.

Best shown in FIGS. 10 and 11, the kinematic mounting assembly 100 further comprises a preloading mechanism 126 having a load member 128 arranged to secure the key 102 in engagement with the receiver 104. The preloading mechanism 126 urges the key 102 into engagement with the receiver 104 such that the key 102 is kinematically constrained to the receiver 104 by six points of contact 130 with the kinematic mounting receiver 104. The preloading mechanism 126 further comprises a shaft 132, a biasing device 134, and a push-button 136. The load member 128 and the push-button 136 are coupled to opposing ends of the shaft 132 with the biasing device 134 arranged therebetween.

The load member 128 is disposed in the preload bore 124 of the receiver 104 and movable between a clamped position and an unclamped position. In the unclamped position, the load member 128 permits the key 102 to be inserted into the cavity 112 of the receiver 104; and in the clamped position, the load member 128 contacts the key 102 urging the key 102 into engagement with the receiver 104. The load member 128 is coupled to one end of a shaft 132 disposed in the preload bore 124 and extending therethrough.

The load member 128 is substantially cylindrical with a first end and a second end. A spherical segment 138 is formed on the first end of the load member 128. The load member 128 may be fixed to the shaft 132 through any suitable mechanism such as a press fit or screw threads. Alternatively, in some examples, the load member 128 may be an integral extension of the shaft 132 or other form of rigid force-applying body attached to the shaft 132.

The biasing device 134 is disposed about the shaft 132 and biases the load member 128 toward the clamped position. In one example, the biasing device 134 is a spring. The spring may have a spring rate of approximately 10 to approximately 25 pounds per inch (lbs/in). Alternatively, the spring may have a spring rate of approximately 20 to approximately 25 lbs/in. Additional spring rates are further contemplated.

The push-button 136 is engageable by the surgeon or user to move the load member 128 toward the unclamped position from the clamped position. The load member 128 and the push-button 136 are fixed to opposite ends of the shaft 132. The push-button 136 is substantially cylindrical and defines a pocket configured to accept the biasing device 134. The push-button 136 may be coupled to the shaft 132 through any suitable mechanism, such as a press fit or screw threads.

FIGS. 4-7 show the key 102 of the kinematic mounting assembly 100. The key 102 comprises two protrusions, a first protrusion 140 and a second protrusion 142. Each protrusion 140, 142 comprises one of the kinematic elements. Each of the protrusions 140, 142 further comprises a pedestal 152, 154 and a clearance channel 144, 146 defined within the respective pedestal 152, 154. Each pedestal 152, 154 comprises a proximal end 172, 174 coupled to the base kinematic element 106 and a distal end 176, 178 coupled to the respective kinematic element 108, 110. Said differently, each pedestal 152, 154 is arranged between the respective kinematic element 108, 110 and the base kinematic element 106. The first protrusion 140 comprises a first pedestal 152 and the second protrusion 142 comprises a second pedestal 154. Each pedestal 152, 154 has a cylindrical cross section that is smaller than the kinematic elements 106, 108, 110.

Each of the first protrusion 140 and the second protrusion 142 further comprises a clearance channel 144, 146 defined within the respective pedestal 152, 154 and within a portion of the respective kinematic element 108, 110. The first protrusion 140 comprises a first clearance channel 144 defined within the first pedestal 152 and within a portion of the first kinematic element 108. The second protrusion 142 comprises a second clearance channel 146 defined within the second pedestal 154 and within a portion of the second kinematic element 110.

As mentioned above, the key 102 comprises three kinematic elements, which are further defined as a base kinematic element 106, a first kinematic element 108, and a second kinematic element 110. Each protrusion 140, 142 is coupled to the base kinematic element 106, and each of the protrusions 140, 142 has a respective kinematic element, the first protrusion 140 having the first kinematic element 108, and the second protrusion 142 having the second kinematic element 110. Said differently, the first protrusion 140 defines the first clearance channel 144 and has the first kinematic element 108, and the second protrusion 142 defines the second clearance channel 146 and has the second kinematic element 110. As used throughout the detailed description, the terms "first" and "second" are used merely to differentiate between each of the protrusions. As will be discussed in further detail below, the first kinematic element 108 and the second kinematic element 110 are configured so that the kinematic mounting key 102 is engageable with the kinematic mounting receiver 104 in both the first arrangement and the second arrangement, the second arrangement being different from the first arrangement.

Each protrusion 140, 142 is coupled to the base kinematic element 106 and extends distally therefrom along a respective axis. Best shown in FIG. 7, the first protrusion 140 defines a first axis 148 extending through the base kinematic element 106 and the first kinematic element 108, and the second protrusion 142 defines a second axis 150 extending through the base kinematic element 106 and the second kinematic element 110. In the example illustrated throughout the drawings, the first axis 148 and the second axis 150 are approximately perpendicular to each other. However, in other examples, the axes may be arranged at an angle other than 90 degrees to each other.

Figure 7:
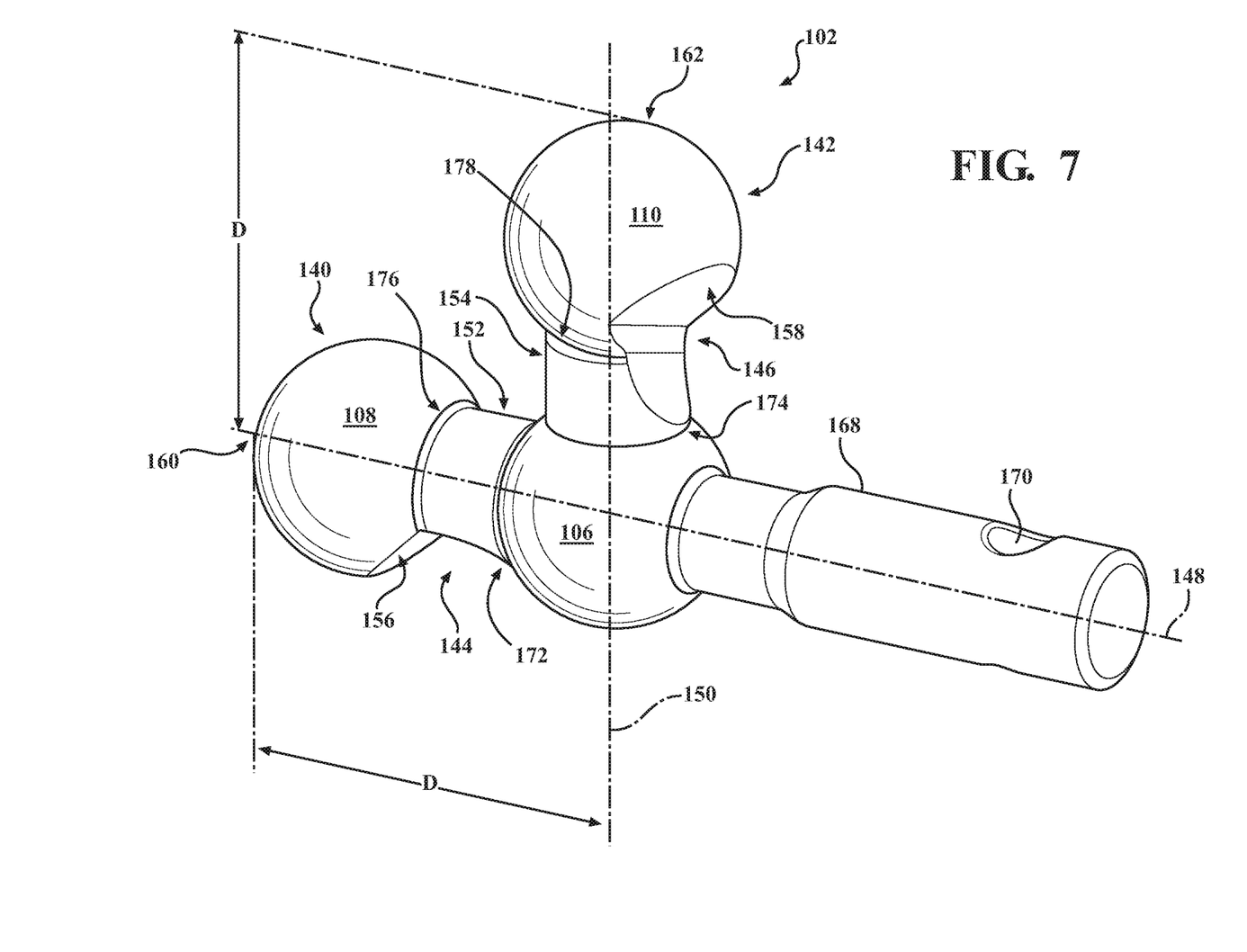
FIG. 7 is a perspective view of the kinematic mounting key.
Figure 8:
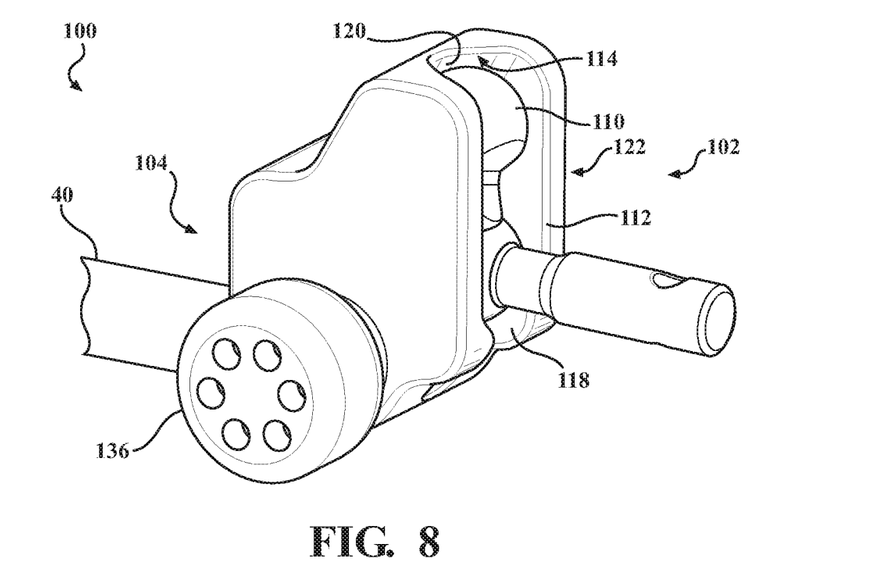
FIG. 8 is a perspective view of the kinematic mounting key engaged in a first position with the kinematic mounting receiver.

Both the first kinematic element 108 and the second kinematic element 110 are spaced from the base kinematic element 106 along the first axis 148 and the second axis 150, respectively. The first kinematic element 108 is spaced from the base kinematic element 106 by the first pedestal 152. The second kinematic element 110 is spaced from the base kinematic element 106 by the second pedestal 154.

In order to accommodate coupling the key 102 to the receiver 104 in both the first and second arrangement, the key 102 must engage the receiver 104 and the preloading mechanism 126 in the same way. To this end, the protrusions 140, 142 are similar to each other; specifically, the first kinematic element 108 has a first distal end 160, and the second kinematic element 110 has a second distal end 162. Shown in FIGS. 4 and 7, each distal end 160, 162 is equally spaced from the base kinematic element 106 along the respective axis 148, 150 such that a distance D can be measured between each distal end 160, 162 and the opposite axis. More specifically, the distance D between the first distal end 160 and the second axis 150 is equal to the distance D between the second distal end 162 and the first axis 148.

Best shown in FIGS. 4-7, the clearance channels 144, 146 are defined within the distal end 176, 178 of each pedestal 152, 154 and within a portion of the respective kinematic element 108, 110. The clearance channels 144, 146 are configured to provide space for operation of the preloading mechanism 126. Each of the first clearance channel 144 and the second clearance channel 146 comprises a loading surface 156, 158 that is engageable with the load member 128 to kinematically constrain the kinematic mounting key 102. The first clearance channel 144 comprises a first loading surface 156, and the second clearance channel 146 comprises a second loading surface 158. The loading surfaces 156, 158 may be partially defined in the respective kinematic element 108, 110. Each clearance channel 144, 146 provides space for the preloading mechanism 126 to engage the loading surfaces 156, 158 from the second channel 118. To this end, each of the clearance channels 144, 146 open toward the preload bore 124 when engaged with the receiver 104 in the respective first and second arrangements.

As mentioned above, the key 102 must engage the receiver 104 and the preloading mechanism 126 the same way in both the first and second arrangements. As such, the loading surfaces 156, 158 are further defined as a first loading surface 156 and a second loading surface 158. Each of the first loading surface 156 and the second loading surface 158 is a flat planar surface that is engageable with the load member 128 at a single point of contact. The loading surfaces 156, 158 are angled at an angle 1 of greater than 90 degrees and less than 180 degrees, and at an angle α of greater than 90 degrees and less than 180 degrees from their respective axis 148, 150. The first loading surface 156 is non-parallel to the second loading surface 158. Because the loading surfaces 156, 158 are angled as such, the first loading surface 156 and the second loading surface 158 are oblique to the first axis 148 and the second axis 150.

The kinematic elements 106, 108, 110 each contact the receiver 104 at the plurality of constraint surfaces 114 such that the key 102 is kinematically constrained to the receiver 104 by being constrained by six points of contact 130 with the receiver 104 (see FIGS. 10 and 11). When the kinematic mounting key 102 is secured in the kinematic mounting receiver 104 in the first arrangement, the kinematic mounting key 102 engages the kinematic mounting receiver 104 at exactly six points of contact 130; and when the kinematic mounting key 102 is secured in the kinematic mounting receiver 104 in the second arrangement, the kinematic mounting key 102 engages the kinematic mounting receiver 104 at exactly six points of contact 130 that are at least partially different from the six points of contact 130 of the first arrangement. Each time the kinematic mounting key 102 is engaged with the kinematic mounting receiver 104 in the first arrangement, each of the kinematic elements 106, 108, 110 contacts the plurality of constraint surfaces 114 at the same six points of contact 130. Likewise, each time the kinematic mounting key 102 is engaged with the kinematic mounting receiver 104 in the second arrangement, each of the kinematic elements 106, 108, 110 contacts the plurality of constraint surfaces 114 at the same six points of contact 130. One or more of the six points of contact 130 resulting from engagement in the first arrangement may be different from the six points of contact 130 resulting from engagement in the second arrangement.

Figure 9:
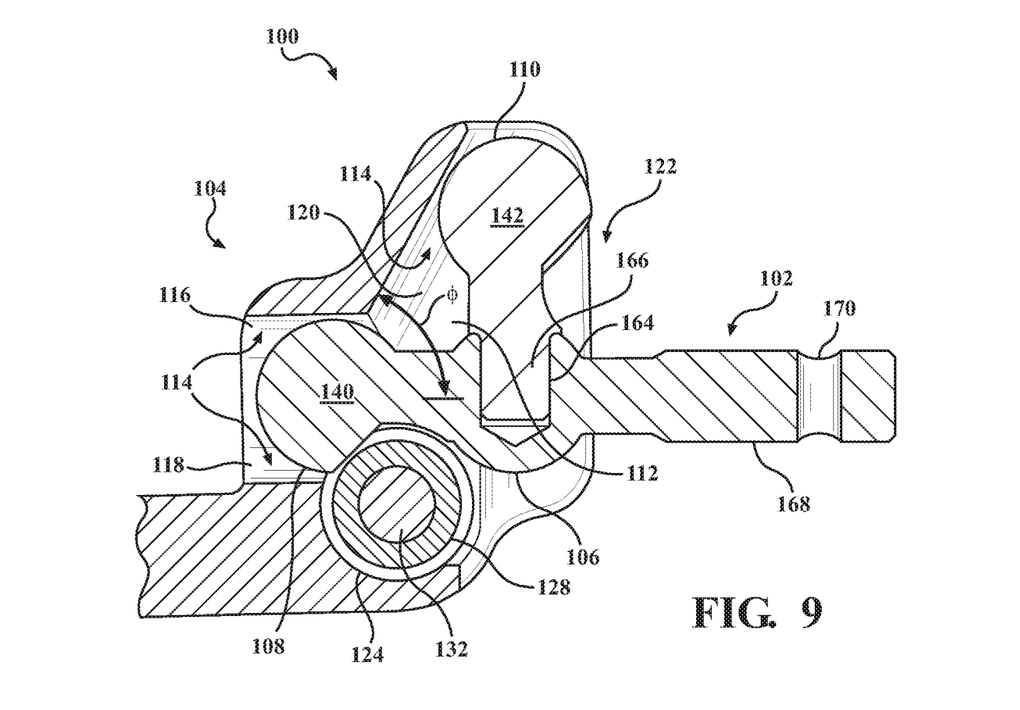
FIG. 9 is a cross-sectional view of the kinematic mounting receiver and the kinematic mounting key of the kinematic mounting assembly of FIG. 8.

Referring to FIG. 9, a cross section of one example of the key 102 engaged with the receiver 104 is shown. Here, the construction of the key 102 can be seen. The first protrusion 140 and the first kinematic element 108 are integrally formed with the base kinematic element 106. The base kinematic element 106 further defines a cross bore 164 extending along the second axis 150 to receive the second protrusion 142. The second protrusion 142 comprises a stem 166 coupled to the proximal end 174 of the pedestal 154 opposite the second kinematic element 110. The stem 166 is engageable with the cross bore 164 for coupling the second protrusion 142 to the base kinematic element 106. In one example, the stem 166 is pressed into the base kinematic element 106 and coupled to the cross bore 164 with an interference fit. In some examples, the second protrusion 142 may be further secured to the base kinematic element 106 by welding.

In other examples, it is possible to construct the key 102 with different manufacturing processes. For example, the second protrusion 142 may be integrally formed with the base kinematic element 106, while the first protrusion 140 is coupled with an interference fit. Alternatively, both of the protrusions 140, 142 may be integrally formed with the base kinematic element 106. It is further contemplated that the cross bore 164 and the stem 166 may comprise screw threads to couple one of the protrusions 140, 142 to the base kinematic element 106.

Figure 4:
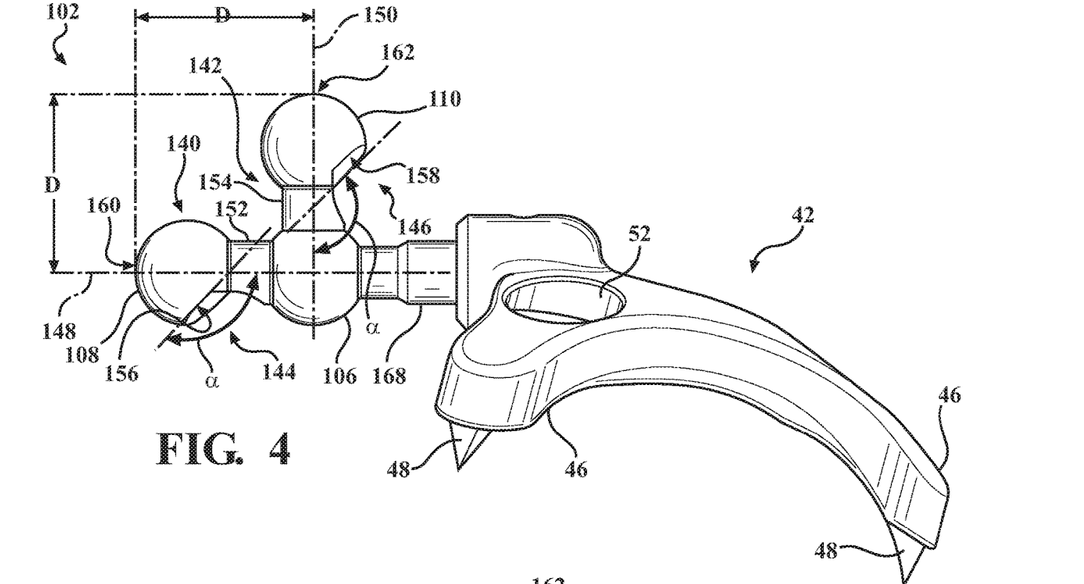
FIG. 4 is a side elevational view of the kinematic mounting key of FIG. 3 coupled to a bone plate.
Figure 5:
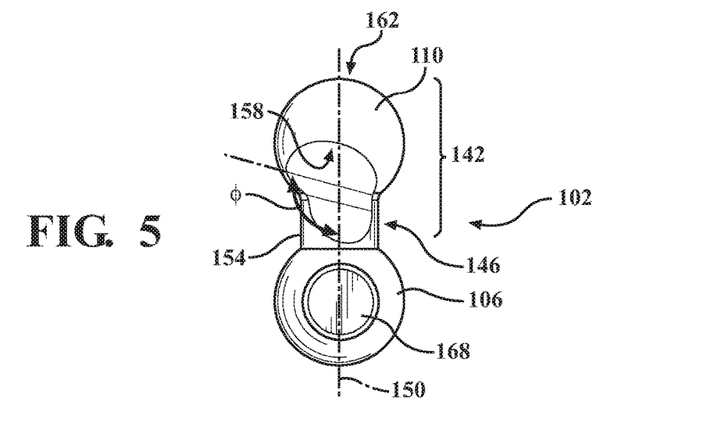
FIG. 5 is a bottom elevational view of the kinematic mounting key of FIG. 4 with the bone plate removed.
Figure 6:
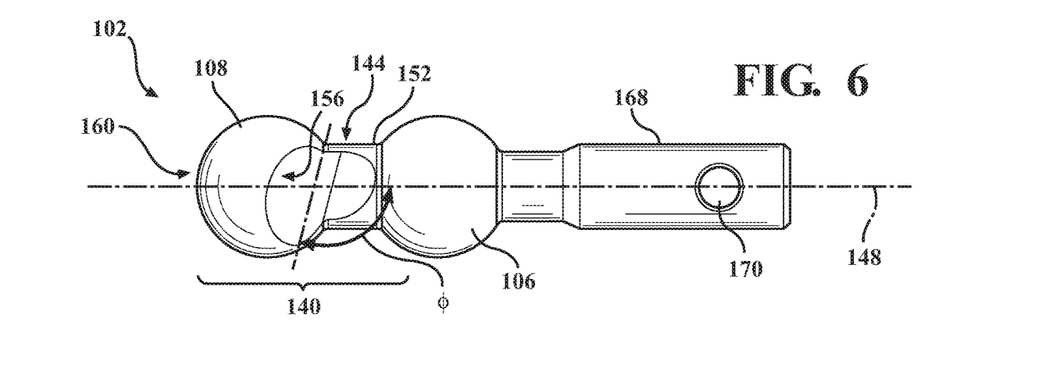
FIG. 6 is a rear elevational view of the kinematic mounting key of FIG. 5 with the bone plate removed.

In order to couple the key 102 to the object to be tracked, a fixation post 168 is coupled to the base kinematic element 106, shown in FIG. 4. The fixation post 168 is engaged with the bone plate 42 to enable the tracker 22 to be affixed to the patient. The fixation post 168 has a circular cross-section that extends away from both the first kinematic element 108 and the second kinematic element 110. Here, the fixation post 168 protrudes from the base kinematic element 106 and along the first axis 148. In the example shown, the fixation post 168 defines a cross hole 170 (FIG. 7) to secure the key 102 to the object to be tracked. A pin (not shown) may be inserted through the assembled fixation post 168 and bone plate 42, preventing the key 102 from being readily removed from the bone plate 42.

Shown in FIGS. 10 and 11, the six points of contact 130 kinematically constrain the key 102 in the receiver 104 by constraining all six degrees of freedom. Each kinematic element/channel engagement constrains two degrees of freedom because of the two points of contact. More specifically, each of the base kinematic element 106, the first kinematic element 108, and the second kinematic element 110 comprises a spherical segment. Engagement between any one of the spherical segments and one of the constraint surfaces 114 of the kinematic mounting receiver 104 is only at a single point of contact. For instance, in the example shown, the base and second kinematic elements 106, 110 are seated in the second and third channels 118, 120, respectively, to constrain four degrees of freedom of the key 102. The first kinematic element 108 is seated in the first channel 116 to constrain the remaining two degrees of freedom of the key 102 in the receiver 104.

In the example illustrated throughout the drawings, the kinematic mounting key 102 has only the base kinematic element 106, the first kinematic element 108, and the second kinematic element 110. However, in other examples, the receiver 104 and key 102 can be configured with additional kinematic elements, such that two kinematic elements each constrain two degrees of freedom, and to other kinematic elements each constrain one degree of freedom, for a total of four kinematic elements that collectively constrain six degrees of freedom. Other configurations are contemplated, so long as exactly six degrees of freedom are constrained.

Because the key 102 is constrained at exactly six points of contact 130 in the receiver 104, the key 102 will always be coupled to the receiver 104 in the same position and orientation relative to the receiver 104. This allows the key 102 to be de-coupled from and coupled to the receiver 104 in a known position such that the connection is repeatable and deterministic.

The preloading mechanism 126 secures the key 102 in the receiver 104 so as to be fully constrained by directing each kinematic element 106, 108, 110 to contact the receiver 104 at exactly two points. As shown in FIGS. 9-11 the first kinematic element 108 is inserted into the cavity 112 of the receiver 104 and seated in the first channel 116. The base and second kinematic elements 106, 110 are inserted in the mouth portion 122 of the cavity 112, with the base kinematic element 106 seated in the second channel 118 and the second kinematic element 110 seated in the third channel 120.

Referring to FIGS. 2, 3, 10, and 11, the first and second arrangements of the kinematic mounting assembly 100 are shown. In this example, the extension link 40 is shown coupled to the receiver 104 opposite to the mouth portion 122 of the cavity 112. The extension link 40 is approximately parallel with the first and second channels 116, 118 of the receiver 104. In FIG. 10, the first arrangement of the kinematic mounting assembly 100 is shown, where the key 102 is engaged with the receiver 104 such that the extension link 40 is approximately parallel with the first axis 148 of the key 102. In FIG. 11, the second arrangement of the kinematic mounting assembly 100 is shown, where the key 102 is engaged with the receiver 104 such that the extension link 40 is approximately parallel with the second axis 150 of the key 102. Transitioning the key 102 between engagement in the first arrangement and engagement in the second arrangement rotates the key 102 relative to the receiver 104. The key 102 is rotated 180 degrees about one of the first axis and the second axis between the first arrangement and the second arrangement.

When the key 102 is engaged with the receiver 104, the spherical segment 138 of the load member 128 contacts one of the loading surfaces 156, 158 of the key 102. Owing to the spring force of the biasing device 134, a force is generated that urges the key 102 into the receiver 104. The angle Φ of the loading surface 156, 158 allows the load member 128 to exert a force that urges the key 102 into the receiver 104, as well as into a fully constrained position with exactly six points of contact 130 with the receiver 104. The spherical segment 138 can only apply force perpendicular to the loading surface 156, 158. Because the spherical segment 138 of the load member 128 acts against the planar loading surface 156, 158, the key 102 does not become over-constrained in the receiver 104. The angle 1 is also such that the kinematic mounting assembly 100 is not back-drivable. For example, a pull-out force on the key 102 increases frictional force on the loading surface 156, 158, preventing the load member 128 from moving to the unclamped position.

The kinematic mounting assembly 100 described herein may be used for connecting together other surgical components. For example, the kinematic mounting assembly 100 may be used to couple a tracker to a powered instrument such as a high-speed drill. The kinematic mounting key 102 may be coupled to, or integrally formed on, the powered instrument to mount a tracker head 38. Likewise, surgical hand tools may also include a kinematic mounting key 102 that is engageable with the kinematic mounting receiver 104 of the tracker head 38. As with above, the ability to couple the key 102 and the receiver 104 in more than one arrangement may be used to advantageously configure both the powered instruments and hand tools. For example, the surgeon could position the tracker head 38 to protrude perpendicular to the tool to optimize visibility to the localizer, or parallel to the tool to enhance the surgeon's visibility of the surgical site. The kinematic mounting assembly 100 may also be used in combination with a robotic surgical system to attach a tracker head 38 to a robotic arm and/or an end effector.

Several examples have been discussed in the foregoing description. However, the examples discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A kinematic mounting key engageable with a kinematic mounting receiver, the kinematic mounting key comprising:
   a base kinematic element;
   a first protrusion comprising:
   a first pedestal comprising a proximal end and a distal end, said proximal end coupled to said base kinematic element;
   a first kinematic element coupled to said distal end of said first pedestal; and
   a first clearance channel defined within said first pedestal and within a portion of said first kinematic element, said first clearance channel comprising a first flat planar surface; and
   a second protrusion comprising:
   a second pedestal comprising a proximal end and a distal end, said proximal end coupled to said base kinematic element;
   a second kinematic element coupled to said distal end of said second pedestal; and
   a second clearance channel defined within said second pedestal and within a portion of said second kinematic element, said second clearance channel comprising a second flat planar surface.

2. The kinematic mounting key of claim 1, wherein said first kinematic element and said second kinematic element are configured so that the kinematic mounting key is engageable with the kinematic mounting receiver in a first arrangement and in a second arrangement that is different from said first arrangement.

3. The kinematic mounting key of claim 2, wherein the kinematic mounting key is engageable with the kinematic mounting receiver at exactly six points of contact in said first arrangement, and in said second arrangement the kinematic mounting key is engageable with the kinematic mounting receiver at exactly six points of contact that are at least partially different from the six points of contact of said first arrangement.

4. The kinematic mounting key of claim 1, wherein said first protrusion defines a first axis extending through said base kinematic element and said first kinematic element, and wherein said second protrusion defines a second axis extending through said base kinematic element and said second kinematic element, said first axis and said second axis being perpendicular to each other.

5. The kinematic mounting key of claim 4, wherein said first kinematic element has a first distal end and said second kinematic element has a second distal end, and wherein a distance between said first distal end and said second axis is equal to a distance between said second distal end and said first axis.

6. The kinematic mounting key of claim 4, wherein said first flat planar surface is further defined as a first loading surface and said second flat planar surface is further defined as a second loading surface.

7. The kinematic mounting key of claim 6, wherein said first flat planar surface of said first loading surface is oblique to said first axis and said second axis, and said second flat planar surface of said second loading surface is oblique to said first axis and said second axis.

8. The kinematic mounting key of claim 6, wherein said first flat planar surface of said first loading surface and said second flat planar surface of said second loading surface are non-parallel to each other.

9. The kinematic mounting key of claim 1, wherein each of said base kinematic element, said first kinematic element, and said second kinematic element comprises a spherical segment.

10. The kinematic mounting key of claim 1, wherein said first protrusion is integrally formed with said base kinematic element.

11. The kinematic mounting key as set forth in claim 1, wherein said base kinematic element defines a cross bore and said second protrusion comprises a stem coupled to said proximal end of said second pedestal and engageable with said cross bore to couple said second protrusion to said base kinematic element.

12. The kinematic mounting key as set forth in claim 1, wherein the kinematic mounting key is coupled to one of a surgical navigation tracker, a surgical guide component, a powered surgical instrument component, a surgical hand tool component, and a surgical robot component.

13. A kinematic mounting assembly comprising:
a kinematic mounting receiver defining a cavity and having a first pair of constraint surfaces and a second pair of constraint surfaces accessible in said cavity;
a kinematic mounting key engageable with said kinematic mounting receiver, said kinematic mounting key comprising:
a base kinematic element;
a first protrusion comprising a first pedestal comprising a proximal end and a distal end, said proximal end coupled to said base kinematic element, a first kinematic element coupled to said distal end of said first pedestal, and comprising a first clearance channel defined within said first pedestal and within a portion of said first kinematic element, said first clearance channel comprising a first planar surface; and
a second protrusion comprising a second pedestal comprising a proximal end and a distal end, said proximal end coupled to said base kinematic element, a second kinematic element coupled to said distal end of said second pedestal, and comprising a second clearance channel defined within said second pedestal and within a portion of said second kinematic element, said second clearance channel comprising a second planar surface;
wherein said kinematic mounting key is engageable with said kinematic mounting receiver in a first arrangement and in a second arrangement that is different from said first arrangement; and
a preloading mechanism operably attached to said kinematic mounting receiver and engageable with said first clearance channel to secure said kinematic mounting key to said kinematic mounting receiver in said first arrangement, and further engageable with said second clearance channel to secure said kinematic mounting key to said kinematic mounting receiver in said second arrangement.

14. The kinematic mounting assembly of claim 13, wherein said kinematic mounting key is engageable with said kinematic mounting receiver at exactly six points of contact in said first arrangement, and in said second arrangement said kinematic mounting key is engageable with said kinematic mounting receiver at exactly six points of contact that are at least partially different from the six points of contact of said first arrangement.

15. The kinematic mounting assembly of claim 14, wherein said first arrangement of said kinematic mounting key is further defined by said first kinematic element being engaged with said first pair of constraint surfaces of said kinematic mounting receiver, and said second kinematic element being engaged with said second pair of constraint surfaces of said kinematic mounting receiver, and said second arrangement of said kinematic mounting key is further defined by said first kinematic element being engaged with said second pair of constraint surfaces of said kinematic mounting receiver, and said second kinematic element being engaged with said first pair of constraint surfaces of said kinematic mounting receiver.

16. The kinematic mounting assembly of claim 13, wherein said kinematic mounting key is coupled to a first surgical component, which is defined as one of a surgical navigation tracker, a surgical guide component, a powered surgical tool component, a surgical hand tool component, and a surgical robot component, and wherein said kinematic mounting receiver is coupled to a second surgical component, which is defined as one of a surgical navigation tracker, a surgical guide component, a powered surgical instrument component, a surgical hand tool component, and a surgical robot component.

17. A surgical assembly comprising:
a first surgical component comprising a kinematic mounting receiver defining a cavity and having a first pair and a second pair of constraint surfaces accessible in said cavity;
a second surgical component comprising a kinematic mounting key engageable with said kinematic mounting receiver, said kinematic mounting key comprising:
a base kinematic element;
a first protrusion comprising a first pedestal comprising a proximal end and a distal end, said proximal end coupled to said base kinematic element, a first kinematic element coupled to said distal end of said first pedestal, and comprising a first clearance channel defined within said first pedestal and within a portion of said first kinematic element, said first clearance channel having a first flat planar surface; and
a second protrusion comprising a second pedestal comprising a proximal end and a distal end, said proximal end coupled to said base kinematic element, a second kinematic element coupled to said distal end of said second pedestal, and comprising a second clearance channel defined within said second pedestal and within a portion of said second kinematic element, said second clearance channel having a second flat planar surface.

18. The surgical assembly of claim 17, wherein said first surgical component is further defined as one of a surgical navigation tracker, a surgical guide component, a powered surgical instrument component, a surgical hand tool component, and a surgical robot component; and said second surgical component is further defined as one of a surgical navigation tracker, a surgical guide component, a powered surgical instrument component, a surgical hand tool component, and a surgical robot component.

\* \* \* \* \*